United States Patent
Matsuura et al.

(10) Patent No.: US 11,363,969 B2
(45) Date of Patent: Jun. 21, 2022

(54) EXERCISE INTENSITY ESTIMATION METHOD, EXERCISE INTENSITY ESTIMATION DEVICE, AND PROGRAM

(71) Applicant: Nippon Telegraph and Telephone Corporation, Tokyo (JP)

(72) Inventors: Nobuaki Matsuura, Tokyo (JP); Yuichi Higuchi, Tokyo (JP); Hiroyoshi Togo, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 48 days.

(21) Appl. No.: 17/046,061

(22) PCT Filed: Apr. 9, 2019

(86) PCT No.: PCT/JP2019/015430
§ 371 (c)(1),
(2) Date: Oct. 8, 2020

(87) PCT Pub. No.: WO2019/198704
PCT Pub. Date: Oct. 17, 2019

(65) Prior Publication Data
US 2021/0030311 A1 Feb. 4, 2021

(30) Foreign Application Priority Data
Apr. 10, 2018 (JP) .............................. JP2018-075230

(51) Int. Cl.
*A61B 5/352* (2021.01)
*A61B 5/11* (2006.01)
*A61B 5/0245* (2006.01)

(52) U.S. Cl.
CPC .......... *A61B 5/1118* (2013.01); *A61B 5/0245* (2013.01); *A61B 5/352* (2021.01)

(58) Field of Classification Search
None
See application file for complete search history.

(56) References Cited

U.S. PATENT DOCUMENTS 4,622,980 A * 11/1986 Kunig ................... A61B 5/222
600/517
7,909,764 B1   3/2011 Wenzel et al.

FOREIGN PATENT DOCUMENTS

| JP | 2004275281 A | 10/2004 |
| WO | 2016166757 A1 | 10/2016 |
| WO | WO-2017121729 A1 * | 7/2017 ......... A61B 5/02405 |

OTHER PUBLICATIONS

Xu, et al., "ECG and Pulse Variability Analysis for Exercise Evaluation," Proceeding of the IEEE, International Conference on Automation and Logistics, Chongqing, China, Aug. 2011, pp. 52-57.

* cited by examiner

*Primary Examiner* — Ankit D Tejani
(74) *Attorney, Agent, or Firm* — Slater Matsil, LLP (57) ABSTRACT

An exercise intensity estimation apparatus includes an RS wave calculation unit configured to calculate an RS amplitude from a peak value of an R wave to a peak value of an S wave in an ECG waveform of a target person, a T wave calculation unit configured to calculate an amplitude of a T wave of the ECG waveform, a heart rate calculation unit configured to calculate a heart rate from the ECG waveform, an index calculation unit configured to calculate, as a first index indicating exercise intensity of the target person, the amplitude of the T wave normalized by the RS amplitude, and an index calculation unit configured to calculate, as a second index indicating the exercise intensity of the target person, a value obtained by multiplying the first index by the heart rate.

7 Claims, 10 Drawing Sheets

EXERCISE INTENSITY ESTIMATION METHOD, EXERCISE INTENSITY ESTIMATION DEVICE, AND PROGRAM

CROSS-REFERENCE TO RELATED APPLICATIONS

This application is a national phase entry of PCT Application No. PCT/JP2019/015430, filed on Apr. 9, 2019, which claims priority to Japanese Application No. 2018-075230, filed on Apr. 10, 2018, which applications are hereby incorporated herein by reference.

TECHNICAL FIELD

The present invention relates to an exercise intensity estimation method, exercise intensity estimation apparatus, and program for estimating exercise intensity from the electrocardiographic waveform of the human.

BACKGROUND

In recent years, a wearable ECG (Electrocardiogram) waveform measurement device that incorporates an electrode in clothing such as a shirt has been developed, and used in various scenes.

If an ECG waveform can be measured, it is possible to acquire various kinds of biological information. For example, if exercise intensity exceeds a predetermined degree in sport training or the like, it is necessary to increase a blood flow to the body, and thus the heart increases the heart rate and also increases a ventricular end-diastolic volume (preload reserve). In this case, in an ECG waveform, the profile of a T wave corresponding to ventricular diastole is considered to change. Therefore, analysis of the T wave can be used for estimation of exercise intensity and the like.

However, in the wearable ECG waveform measurement device, the amplitude level of an ECG waveform may vary depending on the degree of wetting of the electrode or the condition of contact with the body surface. In this case, the height of a T wave also varies in accordance with the amplitude level, and it becomes difficult to correctly evaluate the influence of exercise intensity.

Patent literature 1 discloses an arrangement of evaluating exercise intensity based on a change of the relaxation time of the heart, that is, a change of the length of a T wave. However, the arrangement disclosed in patent literature 1 does not consider a variation in amplitude level of an ECG waveform.

RELATED ART LITERATURE

Patent Literature

Patent Literature 1: Japanese Patent Laid-Open No. 2004-275281.

SUMMARY

Problem to be Solved by Embodiments of the Invention

Embodiments of the present invention have been made in consideration of the above problem, and has as its object to provide an exercise intensity estimation method, exercise intensity estimation apparatus, and program capable of obtaining an appropriate index indicating exercise intensity even when the amplitude of an ECG waveform varies.

Means of Solution to the Problem

According to embodiments of the present invention, there is provided an exercise intensity estimation method comprising a first step of calculating one of an RS amplitude from a peak value of an R wave to a peak value of an S wave in an electrocardiographic waveform of a target person, a height of the R wave, and a depth of the S wave, a second step of calculating one of an amplitude and a height of a T wave of the electrocardiographic waveform, and a third step of calculating, as a first index indicating exercise intensity of the target person, a value obtained by normalizing one of the amplitude and the height of the T wave using one of the RS amplitude, the height of the R wave, and the depth of the S wave.

One arrangement example of the exercise intensity estimation method according to embodiments of the present invention is further comprising a fourth step of calculating a heart rate from the electrocardiographic waveform, and a fifth step of calculating, as a second index indicating the exercise intensity of the target person, a value obtained by multiplying the first index by the heart rate.

According to embodiments of the present invention, there is also provided an exercise intensity estimation apparatus comprising a first calculation unit configured to calculate one of an RS amplitude from a peak value of an R wave to a peak value of an S wave in an electrocardiographic waveform of a target person, a height of the R wave, and a depth of the S wave, a second calculation unit configured to calculate one of an amplitude and a height of a T wave of the electrocardiographic waveform, and a third calculation unit configured to calculate, as a first index indicating exercise intensity of the target person, a value obtained by normalizing one of the amplitude and the height of the T wave using one of the RS amplitude, the height of the R wave, and the depth of the S wave.

According to embodiments of the present invention, there is also provided an exercise intensity estimation program causing a computer to execute a first step of calculating one of an RS amplitude from a peak value of an R wave to a peak value of an S wave in an electrocardiographic waveform of a target person, a height of the R wave, and a depth of the S wave, a second step of calculating one of an amplitude and a height of a T wave of the electrocardiographic waveform, and a third step of calculating, as a first index indicating exercise intensity of the target person, a value obtained by normalizing one of the amplitude and the height of the T wave using one of the RS amplitude, the height of the R wave, and the depth of the S wave.

Effect of Embodiments of the Invention

According to embodiments of the present invention, it is possible to properly grasp a change of a T wave. Even if the amplitude of the electrocardiographic waveform of a target person varies, it is possible to obtain an appropriate index indicating the exercise intensity of the target person. According to embodiments of the present invention, even if a wearable waveform measurement device is used, it is possible to obtain an appropriate index. As a result, in embodiments of the present invention, it is possible to correctly estimate the exercise intensity of the target person.

DETAILED DESCRIPTION OF ILLUSTRATIVE EMBODIMENTS

An embodiment of the present invention will be described below with reference to the accompanying drawings.

Figure 1:
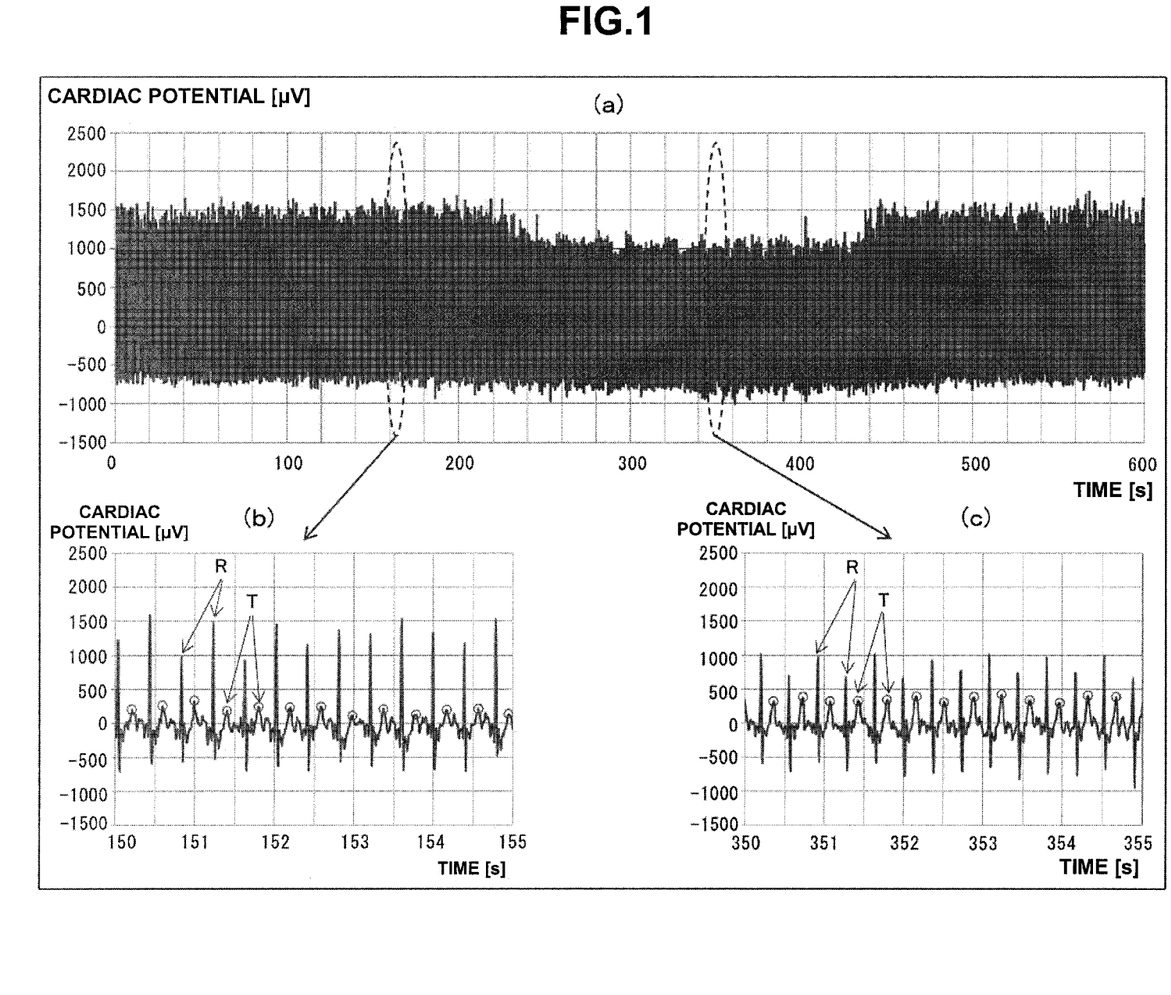
FIG. 1 shows timing charts of an example of an ECG waveform.

FIG. 1 shows timing charts of the ECG waveform of a subject acquired using a wearable device when the subject is running. In a timing chart (for 600 sec) shown in (a) of FIG. 1, in a section of about 220 to 440 sec on the abscissa, the amplitude level of the ECG waveform lowers for some reason.

In FIG. 1, (b) is obtained by enlarging a portion at about 150 sec of the timing chart shown in (a) of FIG. 1, and (c) is obtained by enlarging a portion at about 350 sec of the timing chart shown in (a) of FIG. 1. Each ○ mark in each of (b) and (c) of FIG. 1 indicates the position of a peak of a T wave. Referring to (b) and (c) of FIG. 1, the amplitude level of an R wave at about 350 sec lowers, as compared with that at about 150 sec. Therefore, it is indicated that the relative relationship with the amplitude of an R wave should be considered when evaluating the height of a T wave.

Figure 2:
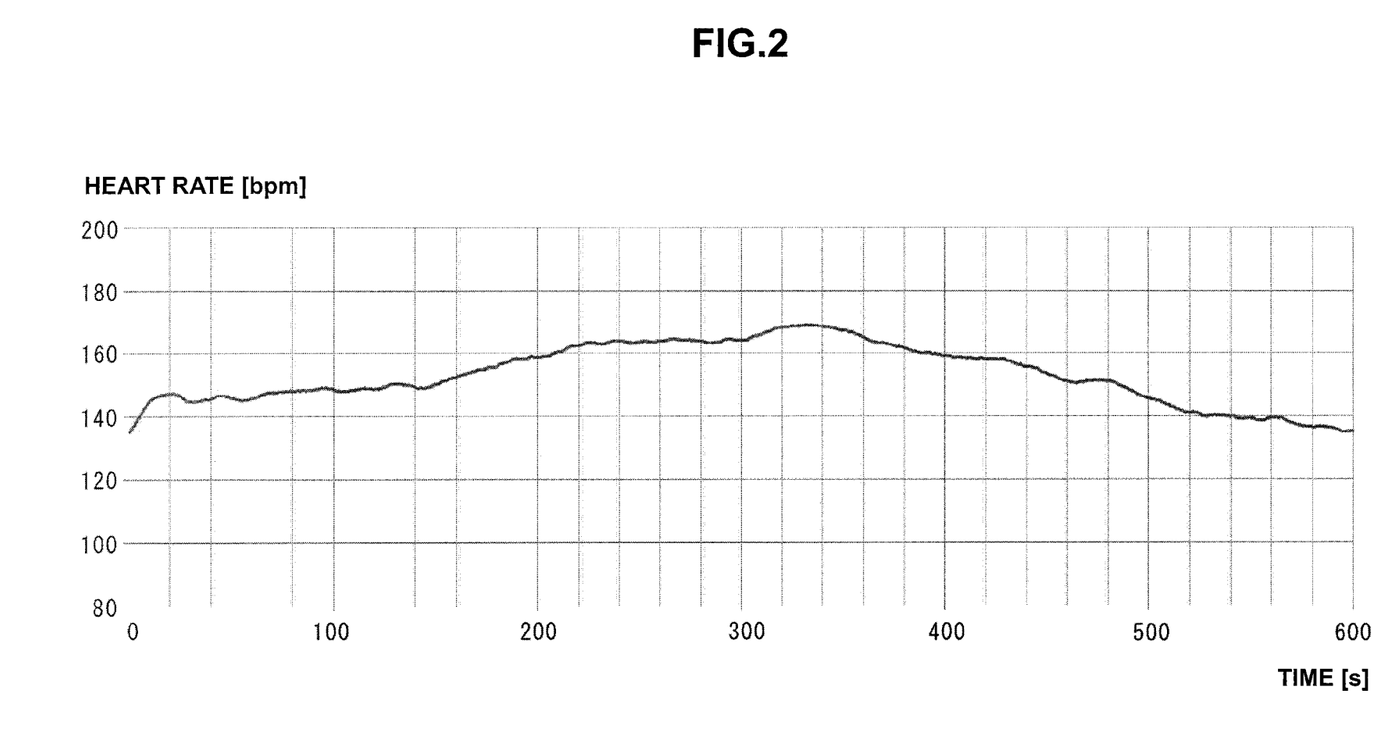
FIG. 2 is a timing chart showing an example of a heart rate.

FIG. 2 is a timing chart showing the heart rate of the subject during the same measurement period as in (a) of FIG. 1. Referring to FIG. 2, the heart rate in a section of 220 to 440 sec is high, and there is a peak at about 330 sec. Exercise intensity can thus be estimated to be highest at about 330 sec.

As described above, the height of a T wave corresponds to a ventricular end-diastolic volume, and is considered as an index that reflects, from an aspect different from the heart rate, the load imposed on the heart, that is, exercise intensity imposed on the subject. However, it is necessary to perform evaluation appropriately in consideration of a variation in amplitude level of the ECG waveform.

Figure 3:
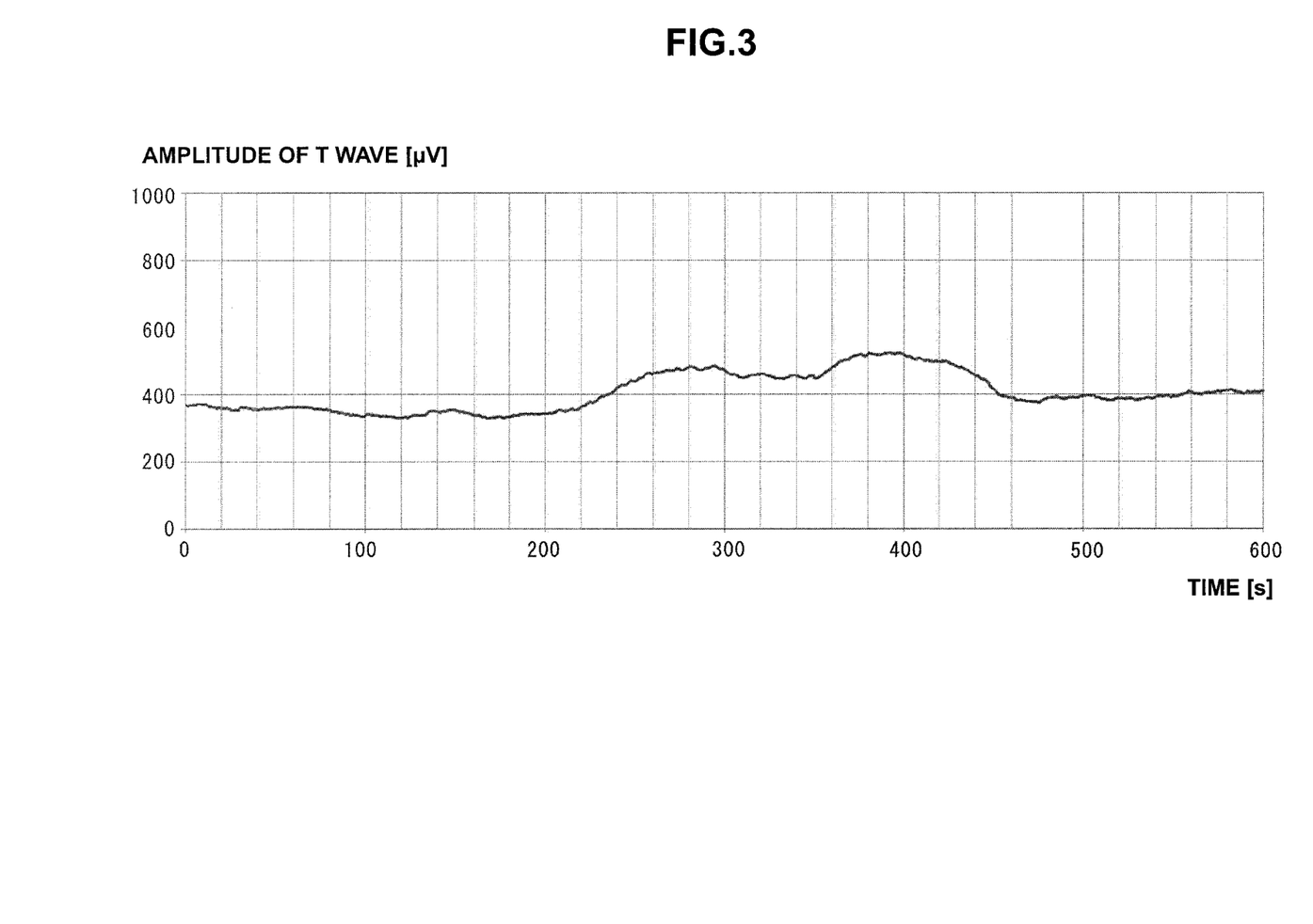
FIG. 3 is a timing chart obtained by plotting the amplitude of a T wave in the ECG waveform.

FIG. 3 is a timing chart obtained by plotting the amplitude of a T wave in the ECG waveform shown in (a) of FIG. 1. The amplitude of the T wave can be obtained by, for example, a method of detecting an R wave from the ECG waveform, detecting the maximum and minimum values in a predetermined time width following the R wave, and obtaining the difference between the maximum and minimum values.

Figure 4:
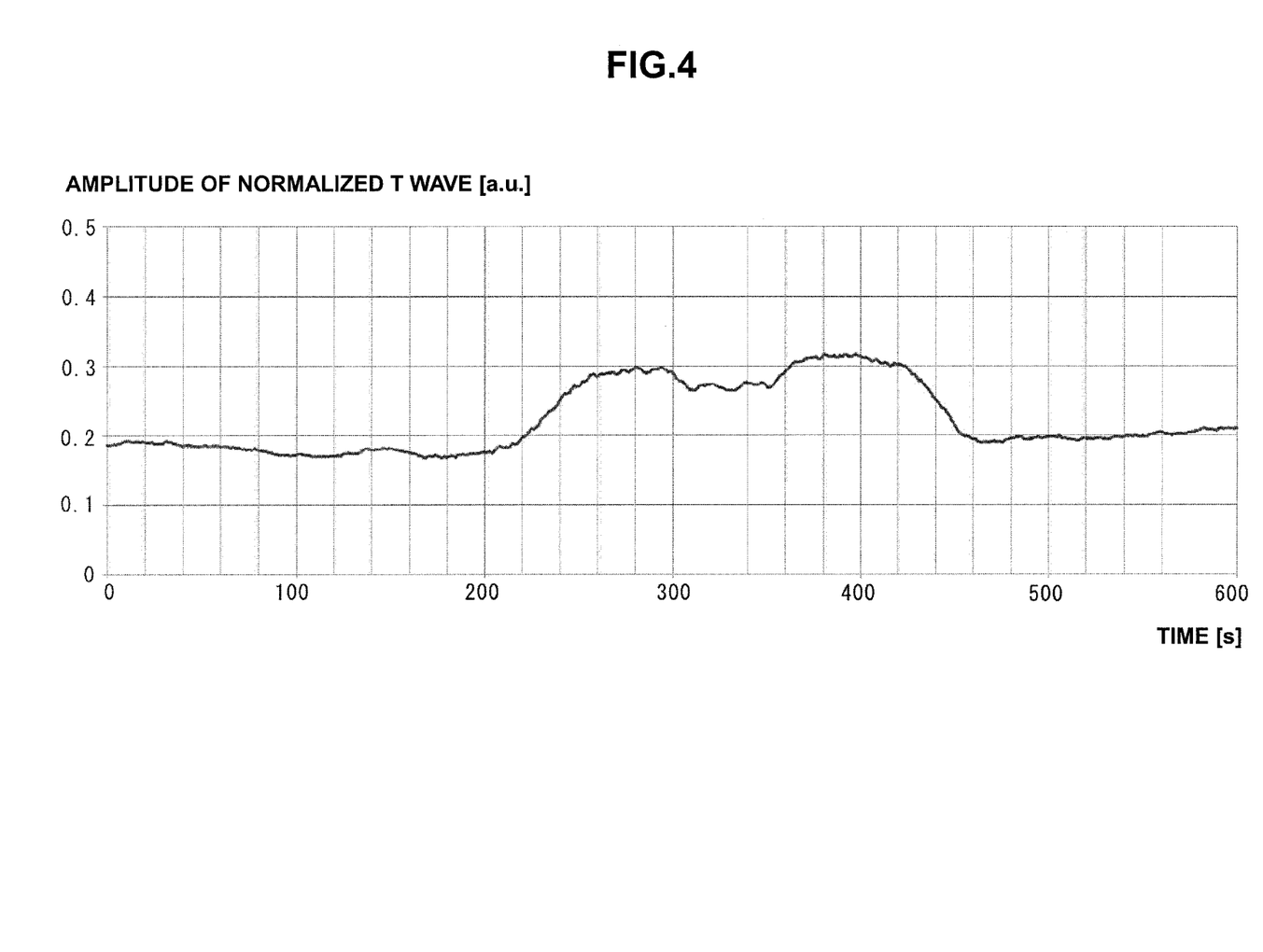
FIG. 4 is a timing chart obtained by plotting the amplitude of a T wave normalized by an RS amplitude in the ECG waveform.

On the other hand, FIG. 4 is a timing chart obtained by plotting a value obtained by dividing the amplitude of a T wave shown in FIG. 3 by the RS amplitude of the same heartbeat as that of the T wave, that is, the amplitude of the T wave normalized by the RS amplitude. In this example, to obtain a smooth curve by excluding the influence of noise of the ECG waveform, each of the RS amplitude and the amplitude of the T wave is resampled at an interval of 0.5 sec, and a moving average for 30 sec is obtained.

Referring to FIG. 3, the amplitude of the T wave is larger in a section of 220 to 440 sec than in other sections by about 25%. On the other hand, referring to FIG. 4, the amplitude of the normalized T wave is larger in a section of 240 to 440 sec than in other sections by about 50%, and the probability that exercise intensity and activation of the preload reserve of the heart are represented more correctly is high.

By combining the amplitude of the T wave with the heart rate (for example, by multiplying the amplitude of the T wave by the heart rate), it is possible to take in information of the heart rate, thereby giving a new index indicating exercise intensity.

Figure 5:
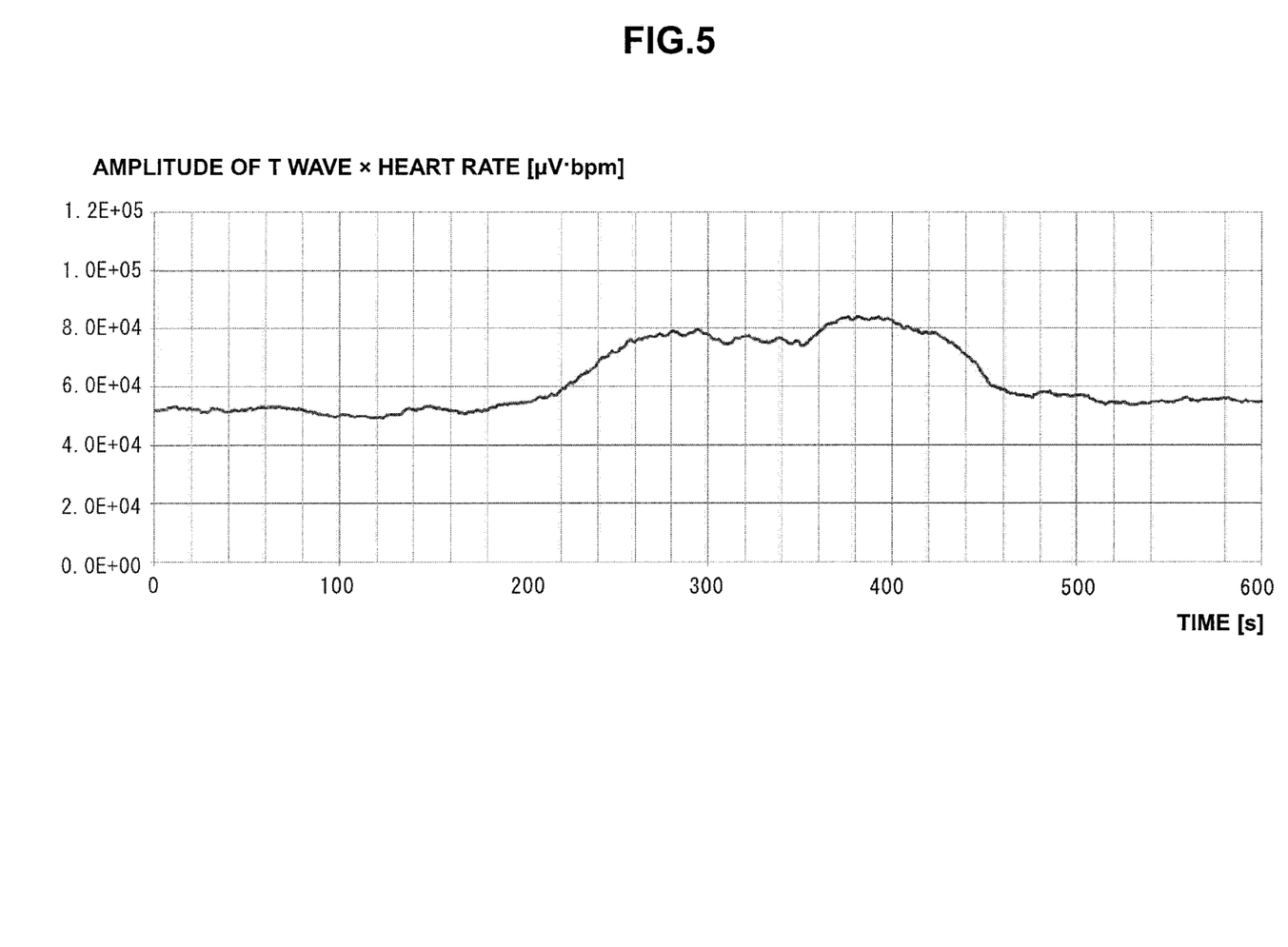
FIG. 5 is a timing chart showing a value obtained by multiplying the amplitude of the T wave in the ECG waveform by the heart rate.
Figure 6:
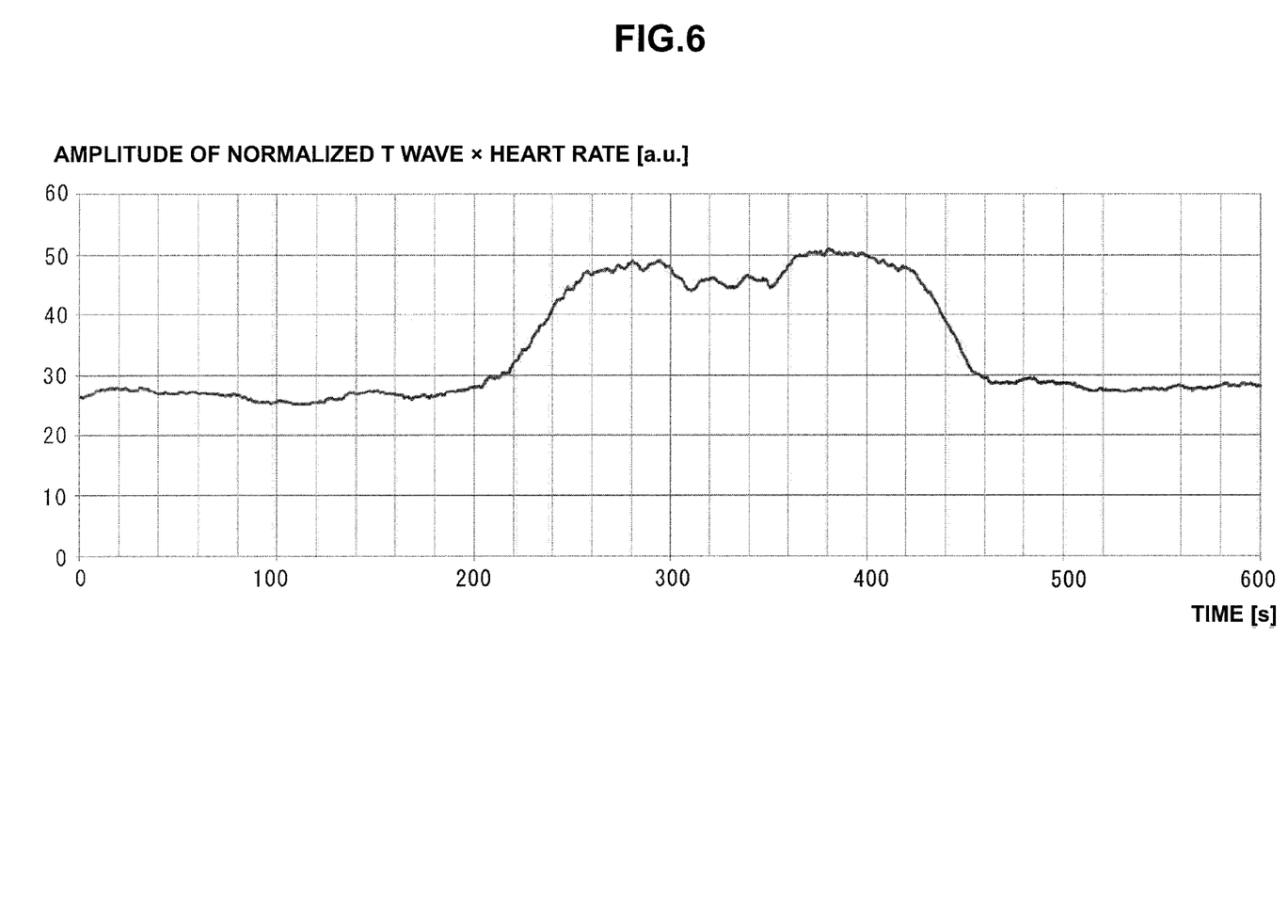
FIG. 6 is a timing chart showing a value obtained by multiplying the amplitude of the normalized T wave in the ECG waveform by the heart rate.

FIG. 5 shows a value obtained by multiplying the amplitude of the T wave shown in FIG. 3 by the heart rate shown in FIG. 2. FIG. 6 shows a value obtained by multiplying the amplitude of the normalized T wave shown in FIG. 4 by the heart rate shown in FIG. 2. Similar to FIGS. 3 and 4, there is the difference between FIGS. 5 and 6. It is considered that evaluation is performed more properly in FIG. 6 with respect to a blood volume ejected by the heart.

Embodiment

Figure 7:
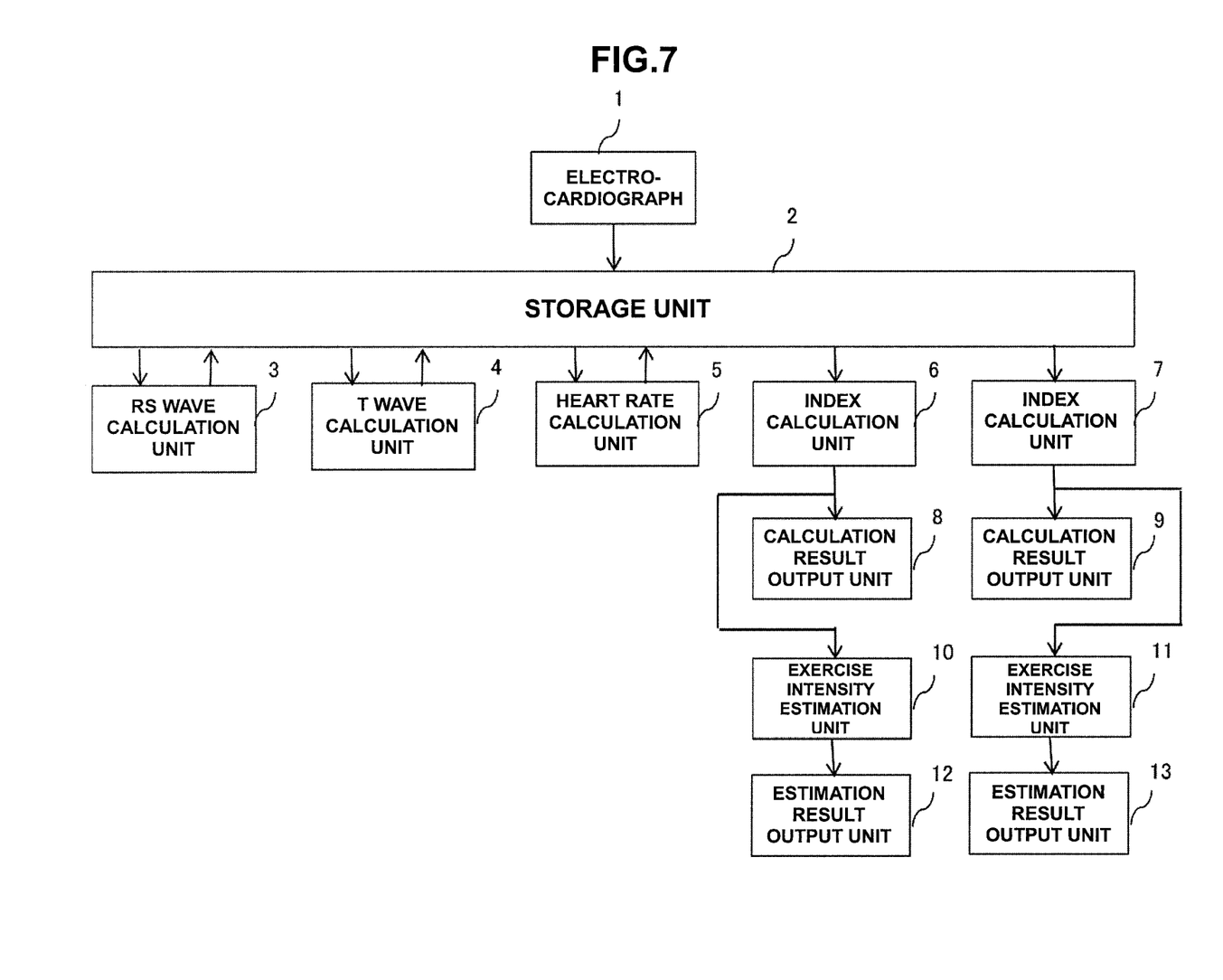
FIG. 7 is a block diagram showing the arrangement of an exercise intensity estimation apparatus according to an embodiment of the present invention.

An embodiment of the present invention will be described below with reference to the accompanying drawings. FIG. 7 is a block diagram showing the arrangement of an exercise intensity estimation apparatus according to the embodiment of the present invention. The exercise intensity estimation apparatus includes an electrocardiograph 1 that outputs the sampling data string of an ECG waveform, a storage unit 2 that stores the sampling data string of the ECG waveform and sampling time information, an RS wave calculation unit 3 (first calculation unit) that calculates an RS amplitude from the peak value of an R wave to the peak value of an S wave in the ECG waveform, a T wave calculation unit 4 (second calculation unit) that calculates the amplitude of a T wave of the ECG waveform, a heart rate calculation unit 5 (fourth calculation unit) that calculates a heart rate from the ECG waveform, an index calculation unit 6 (third calculation unit) that calculates, as the first index indicating the exercise intensity of a target person, the amplitude of the T wave normalized by the RS amplitude, an index calculation unit 7 (fifth calculation unit) that calculates, as the second index indicating the exercise intensity of the target person, a value obtained by multiplying the first index by the heart rate, a calculation result output unit 8 that outputs the calculation result of the index calculation unit 6, a calculation result output unit 9 that outputs the calculation result of the index calculation unit 7, an exercise intensity estimation unit 10 that estimates the exercise intensity of the target person based on the first index, an exercise intensity estimation unit 11 that estimates the exercise intensity of the target person based on the second index, an estimation result output unit 12 that outputs the estimation result of the exercise intensity estimation unit 10, and an estimation result output unit 13 that outputs the estimation result of the exercise intensity estimation unit 11.

Figure 8:
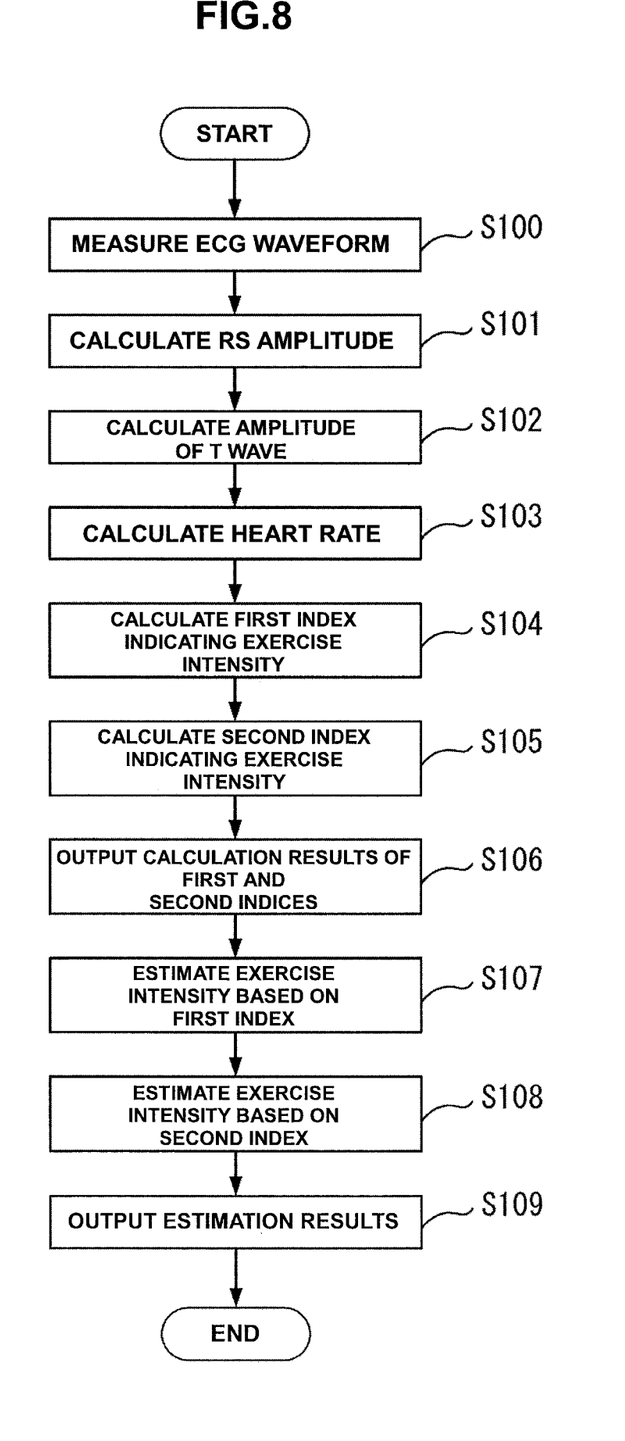
FIG. 8 is a flowchart for explaining the operation of the exercise intensity estimation apparatus according to the embodiment of the present invention.
Figure 9:
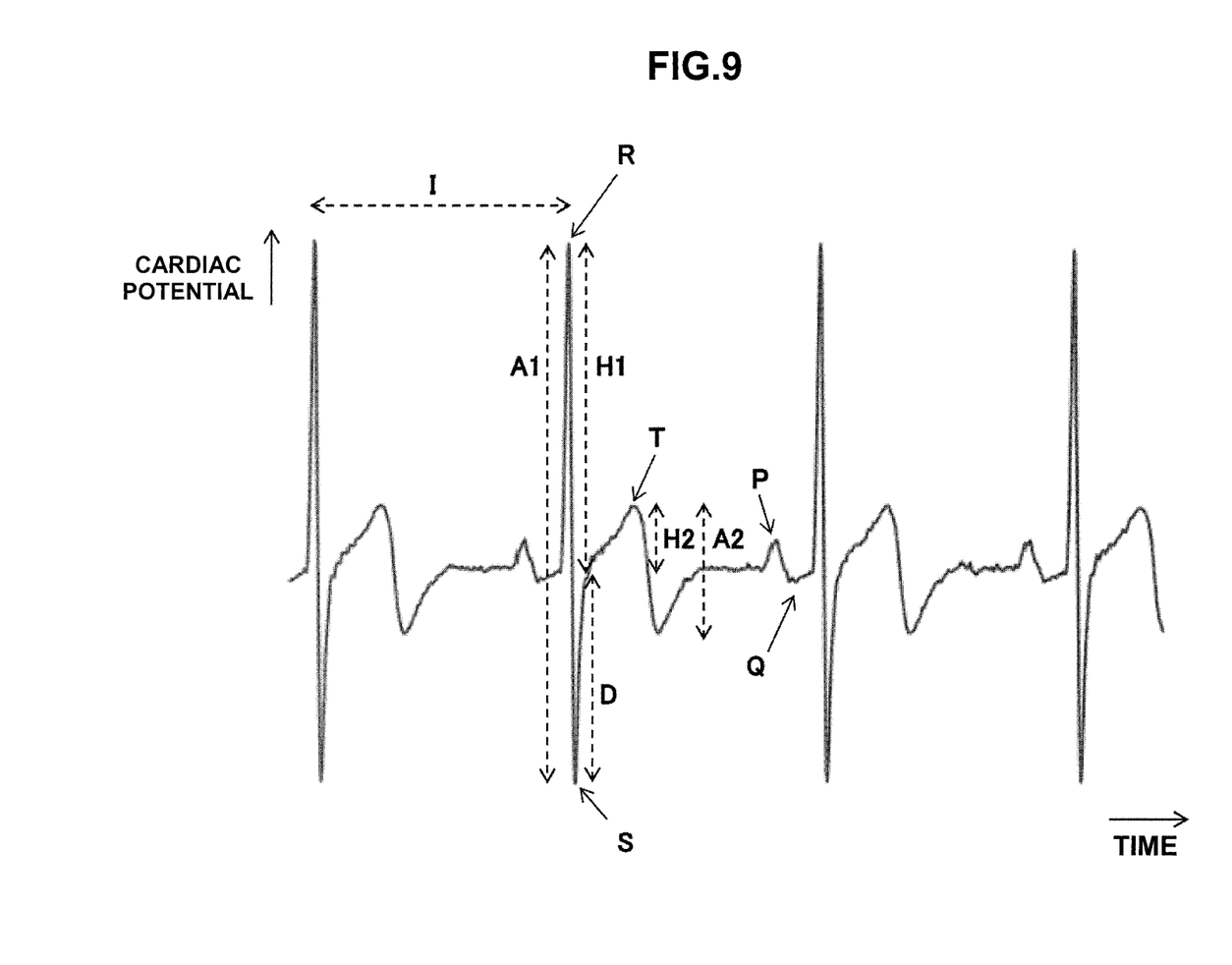
FIG. 9 is a timing chart showing examples of P, Q, R, S, and T waves in an ECG waveform.

The operation of the exercise intensity estimation apparatus according to this embodiment will be described below with reference to FIGS. 8 and 9. FIG. 8 is a flowchart for explaining the operation of the exercise intensity estimation apparatus. FIG. 9 is a timing chart showing examples of P, Q, R, S, and T waves in an ECG waveform.

The electrocardiograph 1 measures the ECG waveform of a target person of exercise intensity estimation, and outputs the sampling data string of the ECG waveform (step S100 in FIG. 8). At this time, the electrocardiograph 1 outputs the sampling data string by adding sampling time information to each sampling data. Note that a practical method of measuring the ECG waveform is a well-known technique, and a detailed description thereof will be omitted. The storage unit 2 stores the sampling data string of the ECG waveform and the sampling time information, which have been output from the electrocardiograph 1.

The RS wave calculation unit 3 calculates, for each heartbeat, an RS amplitude (A1 in FIG. 9) as an amplitude from the peak value of an R wave to the peak value of an immediately succeeding S wave in the ECG waveform stored in the storage unit 2 (step S101 in FIG. 8). Note that a method of detecting the R and S waves is disclosed in, for example, Japanese Patent Laid-Open No. 2015-156936.

The T wave calculation unit 4 calculates, for each heartbeat, the amplitude of a T wave in the ECG waveform stored in the storage unit 2 (step S102 in FIG. 8). More specifically, the T wave calculation unit 4 detects the maximum value (the peak value of the T wave) and the minimum value (the bottom value of the T wave) in a detection period of a predetermined time width after a predetermined standby time elapses since the time of the peak value of the R wave, and calculates the amplitude (A2 in FIG. 9) from the maximum value to the minimum value as the amplitude of the T wave. The standby time is preset so as to remove an S wave immediately after the R wave. Note that the standby time may be determined using, as a starting point, the time of the peak value of the S wave instead of the R wave. The time width of the detection period is preset to include the peak value of the T wave and the bottom value after that.

The heart rate calculation unit 5 calculates, for each heartbeat, a heart rate HR (instantaneous heart rate) from the ECG waveform stored in the storage unit 2 (step S103 in FIG. 8). The heart rate calculation unit 5 detects, for each heartbeat, an R-R interval (I in FIG. 9) as the time interval between an R wave and an immediately preceding R wave, and calculates the heart rate HR for each heartbeat by:

$$HR \text{ [bpm]} = 60000/I \text{ [ms]} \quad (1)$$

The index calculation unit 6 calculate, for each heartbeat, as a first index E1 indicating exercise intensity, an amplitude A2' of the T wave normalized by an RS amplitude A1 (step S104 in FIG. 8). More specifically, the index calculation unit 6 calculates, as the first index E1, a value obtained by dividing an amplitude A2 of the T wave by the RS amplitude A1 (that is, the RS amplitude A1 immediately before the T wave) of the same heartbeat as that of the T wave, by:

$$E1 = A2' = A2/A1 \quad (2)$$

Note that as described in the principles of embodiments of the invention, as the amplitude A2 of the T wave used in equation (2) above, the average value of the amplitude of the T wave in the heartbeat for which the index E1 is to be calculated and the amplitude of the T wave for a past predetermined time (for example, 30 sec) before the heartbeat may be obtained. Similarly, as the RS amplitude A1 used in equation (2) above, the average value of the RS amplitude in the heartbeat for which the index E1 is to be calculated and the RS amplitude for a past predetermined time (for example, 30 sec) before the heartbeat may be obtained.

The index calculation unit 7 calculates, for each heartbeat, as a second index E2 indicating exercise intensity, a value obtained by multiplying the first index E1 by the heart rate HR calculated from the same heartbeat as that of the first index E1 (T wave) (step S105 in FIG. 8), by:

$$E2 = E1 \times HR \quad (3)$$

The calculation result output units 8 and 9 output calculation results obtained by the index calculation units 6 and 7, respectively (step S106 in FIG. 8). As an output method at this time, for example, the graphs of the calculation results are displayed or transmitted to an external device.

The exercise intensity estimation unit 10 estimates the exercise intensity of the target person by comparing the first index E1 calculated by the index calculation unit 6 with a predetermined threshold TH1 (step S107 in FIG. 8). More specifically, if the first index E1 is equal to or smaller than the threshold TH1, the exercise intensity estimation unit 10 estimates that the exercise intensity of the target person is low; otherwise, the exercise intensity estimation unit 10 estimates that the exercise intensity of the target person is high. In the example shown in FIG. 4, for example, the threshold TH1 is set to about 0.25 [a.u.]. Note that a plurality of thresholds TH1 may be provided to perform multistage evaluation of the exercise intensity of the target person.

The exercise intensity estimation unit 11 estimates the exercise intensity of the target person by comparing the second index E2 calculated by the index calculation unit 7 with a predetermined threshold TH2 (step S108 in FIG. 8). More specifically, if the second index E2 is equal to or smaller than the threshold TH2, the exercise intensity estimation unit 11 estimates that the exercise intensity of the target person is low; otherwise, the exercise intensity estimation unit 11 estimates that the exercise intensity of the target person is high. In the example shown in FIG. 6, for example, the threshold TH2 is set to about 40 [a.u.]. Note that a plurality of thresholds TH2 may also be provided to perform multistage evaluation of the exercise intensity of the target person.

The estimation result output units 12 and 13 output the estimation results of the exercise intensity estimation units 10 and 11, respectively (step S109 in FIG. 8). As an output method at this time, for example, the estimation results are displayed, output by voice, or transmitted to an external device.

As described above, in this embodiment, it is possible to properly grasp a change of a T wave. Even if the amplitude of the ECG waveform varies, the appropriate indices E1 and E2 each indicating the exercise intensity of the target person can be obtained. As a result, in this embodiment, it is possible to correctly estimate the exercise intensity of the target person.

Note that embodiments of the present invention are suitable for an ECG waveform measurement device (wearable device) that acquires an ECG waveform by arranging an electrode on the inner surface of clothing such as a shirt and making the electrode contact the body surface of a target person. However, the application target of embodiments of the present invention is not limited to such ECG waveform measurement device.

Figure 10:
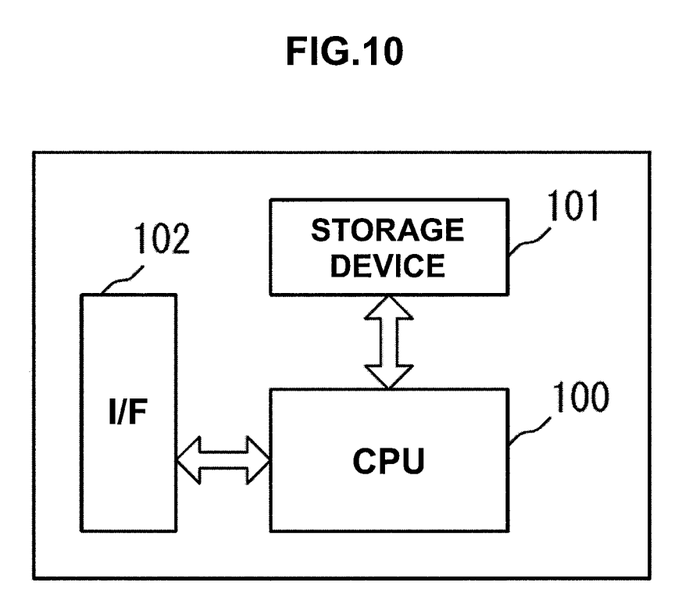
FIG. 10 is a block diagram showing an example of the arrangement of a computer for implementing the exercise intensity estimation apparatus according to the embodiment of the present invention.

The storage unit 2, RS wave calculation unit 3, T wave calculation unit 4, heart rate calculation unit 5, and index calculation units 6 and 7 of the exercise intensity estimation apparatus described in this embodiment can be implemented by a computer including a CPU (Central Processing Unit), a storage device, and an interface, and a program for controlling these hardware resources. FIG. 10 shows an example of the arrangement of this computer. The computer includes a CPU 100, a storage device 101, and an interface device (to be referred to as an I/F hereinafter) 102. The I/F 102 is connected to the electrocardiograph 1 and the hardware components of the calculation result output units 8 and 9. In this computer, an exercise intensity estimation program for implementing the exercise intensity estimation method of embodiments of the present invention is stored in the storage device 101. The CPU 100 executes the processing described in this embodiment in accordance with the exercise intensity estimation program stored in the storage device 101.

Note that in this embodiment, the height (H1 in FIG. 9) of the R wave from the base line of the ECG waveform to the peak value of the R wave may be used instead of the RS amplitude A1. In this case, an R wave calculation unit (first calculation unit) that calculates the height H1 of the R wave for each heartbeat is provided instead of the RS wave calculation unit 3. Alternatively, the depth (D in FIG. 9) of the S wave from the base line of the ECG waveform to the peak value of the S wave may be used instead of the RS amplitude A1. In this case, an S wave calculation unit (first calculation unit) that calculates the depth D of the S wave for each heartbeat is provided instead of the RS wave calculation unit 3. In addition, the height (H2 in FIG. 9) of the T wave from the base line of the ECG waveform to the peak value of the T wave may be used instead of the amplitude A2 of the T wave. In this case, a T wave calculation unit (second calculation unit) that calculates the height H2 of the T wave for each heartbeat is provided instead of the T wave calculation unit 4.

INDUSTRIAL APPLICABILITY

Embodiments of the present invention are applicable to a technique of estimating the exercise intensity of the human.

EXPLANATION OF THE REFERENCE NUMERALS AND SIGNS

1 . . . electrocardiograph, 2 . . . storage unit, 3 . . . RS wave calculation unit, 4 . . . T wave calculation unit, 5 . . . heart rate calculation unit, 6, 7 . . . index calculation unit, 8, 9 . . . calculation result output unit, 10, 11 . . . exercise intensity estimation unit, 12, 13 . . . estimation result output unit.

The invention claimed is:

1. An exercise intensity estimation method comprising:
calculating an RS amplitude from a peak value of an R wave to a peak value of an S wave in an electrocardiographic waveform of a target person, a height of the R wave, or a depth of the S wave;
calculating an amplitude or a height of a T wave of the electrocardiographic waveform;
calculating, as a first index indicating exercise intensity of the target person, a value obtained by normalizing the amplitude or the height of the T wave according to the RS amplitude, the height of the R wave, or the depth of the S wave;
calculating a heart rate from the electrocardiographic waveform; and
calculating, as a second index indicating the exercise intensity of the target person, a value obtained by multiplying the first index by the heart rate.

2. The exercise intensity estimation method according to claim 1, further comprising estimating the exercise intensity of the target person based on the first index.

3. The exercise intensity estimation method according to claim 1, further comprising estimating the exercise intensity of the target person based on the second index.

4. An exercise intensity estimation apparatus comprising:
a first calculator configured to calculate an RS amplitude from a peak value of an R wave to a peak value of an S wave in an electrocardiographic waveform of a target person, a height of the R wave, or a depth of the S wave;
a second calculator configured to calculate one of an amplitude or a height of a T wave of the electrocardiographic waveform;
a third calculator configured to calculate, as a first index indicating exercise intensity of the target person, a value obtained by normalizing the amplitude or the height of the T wave according to the RS amplitude, the height of the R wave, or the depth of the S wave;
a fourth calculator configured to calculate a heart rate from the electrocardiographic waveform; and
a fifth calculator configured to calculate, as a second index indicating the exercise intensity of the target person, a value obtained by multiplying the first index by the heart rate.

5. A non-transitory computer-readable storage medium storing an exercise intensity estimation program causing a computer to execute:
calculating an RS amplitude from a peak value of an R wave to a peak value of an S wave in an electrocardiographic waveform of a target person, a height of the R wave, or a depth of the S wave;
calculating one of an amplitude or a height of a T wave of the electrocardiographic waveform;
calculating, as a first index indicating exercise intensity of the target person, a value obtained by normalizing the amplitude or the height of the T wave according to the RS amplitude, the height of the R wave, or the depth of the S wave;
calculating a heart rate from the electrocardiographic waveform; and
calculating, as a second index indicating the exercise intensity of the target person, a value obtained by multiplying the first index by the heart rate.

6. The non-transitory computer-readable storage medium storing an exercise intensity estimation program according to claim 5, further causing the computer to execute:
estimating the exercise intensity of the target person based on the second index.

7. The non-transitory computer-readable storage medium storing an exercise intensity estimation program according to claim 5, further causing the computer to execute:
estimating the exercise intensity of the target person based on the first index.

* * * * *